United States Patent [19]
Malmin

[11] 4,263,913
[45] Apr. 28, 1981

[54] HAIR REPLACEMENT METHOD

[76] Inventor: Oscar Malmin, 127 W. Wayne Ave., Akron, Ohio 44301

[21] Appl. No.: 932,513

[22] Filed: Aug. 10, 1978

[51] Int. Cl.³ .............................................. A61B 17/00
[52] U.S. Cl. ................................................... 128/330
[58] Field of Search .................. 128/330, 1 R, 340; 3/1; 46/172; 132/5, 56

[56] References Cited
U.S. PATENT DOCUMENTS

| | | | |
|---|---|---|---|
| 527,263 | 10/1894 | Blanchard | 128/339 |
| 1,059,631 | 4/1913 | Popovics | 128/330 |
| 2,253,635 | 8/1941 | Mann | 46/172 |
| 2,636,460 | 4/1953 | Seiderman | 112/1 |
| 3,062,214 | 11/1962 | Maxwell | 128/330 |
| 3,119,398 | 1/1964 | Bennett et al. | 132/5 |
| 3,223,083 | 12/1965 | Cobey | 128/334 R |
| 3,421,521 | 1/1969 | Rich | 132/5 |
| 3,513,860 | 5/1970 | Kost | 132/5 |
| 3,589,376 | 6/1971 | Kohler | 132/5 |
| 3,596,292 | 8/1971 | Erb | 3/1 |
| 3,755,824 | 9/1973 | Sperling | 3/1 |
| 3,845,772 | 11/1974 | Smith | 128/335 |
| 3,877,570 | 4/1975 | Barry | 128/339 |
| 3,908,674 | 9/1975 | Kessler | 132/53 |
| 4,004,592 | 1/1977 | Yamada | 128/330 |
| 4,054,954 | 10/1977 | Nakayama et al. | 3/1 |

FOREIGN PATENT DOCUMENTS

| | | | |
|---|---|---|---|
| 1953026 | 2/1972 | Fed. Rep. of Germany | 3/1 |
| 50-109051 | 8/1975 | Japan | 128/330 |
| 30751 | 5/1920 | Norway | 128/330 |

Primary Examiner—Robert W. Michell
Assistant Examiner—Michael H. Thaler
Attorney, Agent, or Firm—Reese Taylor

[57] ABSTRACT

A method of treating baldness is disclosed which includes the implantation of strands of natural or artificial hair beneath the scalp and into the subcutaneous tissue. The method contemplates pre-forming the strands of hair into a U-shaped loop which can be implaced beneath the scalp by means of a penetration instrument in an arcuate or concave configuration with respect to the scalp for improved retention properties. Apparatus is also disclosed for carrying out the method which will facilitate implanting the hair in the manner just described and which is also capable of disengaging the hair from the penetration instrument for removal of the instrument and which is further capable of injecting tissue adhesives and hemostatic agents into the tissue surrounding the hair to stabilize it and assist the healing and anchoring process. It is also possible to perform the method of this invention without pre-forming the strand except to the extent that it is formed when placed on the penetration instrument.

6 Claims, 16 Drawing Figures

HAIR REPLACEMENT METHOD

FIELD OF THE INVENTION

This invention relates, in general, to a method and apparatus for treating baldness and in particular relates to a method and apparatus wherein the replacement hair can be firmly and securely implanted beneath the scalp to resist inadvertent dislodgement and can be implanted in a particular fashion so that the portions of the replacement hair projecting above the scalp assume natural positions.

PRIOR ART STATEMENT

In general, hairpieces have long been known as one method of solving the problem of baldness. There are also a number of other known treatments and methods of correcting baldness, but problems with poor appearance and defective anchoring have been encountered.

Such methods have involved implanting various retaining devices such as, for example, specially treated wires or sutures into the scalp with portions thereof being exposed and with the exposed portions forming a network to which strands of natural or synthetic hair can be tied or woven. Difficulties have developed with these methods, however, with regard to infection and also to the requirement for periodic tightening or reweaving.

Still further methods have involved cutting a circular plug containing hair follicles from a donor site and transplanting that plug into a prepared recipient site in the bald area. There is a high rate of rejection with this method however.

Additional methods have involved the general concept of embedding synthetic fibers or natural hair into the scalp but a severe problem with regard to anchoring the fibers has been encountered leading to a high failure rate which is believed to be caused by an inability to resist the healing forces for any reasonably long period or due to secondary infection, with a consequent expulsion or rejection of the embedded hair.

With regard to the patent prior art, there are a large number of patents in existence and known to Applicant relating to this general field many of which reflect various of the aforementioned methods.

Bauman U.S. Pat. No. 3,553,737 illustrates one of the "weaving" methods and discloses one of the methods above referred to wherein an anchor member, in the form of a continuous suture, is embedded into the scalp to which a web is attached following which the hair can be attached to the web.

Barry U.S. Pat. No. 3,608,095 is illustrative of the "hairpiece" methods and discloses the placing of loops in the scalp to which a hairpiece can be attached.

Allen U.S. Pat. No. 3,699,969 discloses a hair implant method of one of the types generally referred to above wherein a plug of natural or synthetic fibers is inserted directly into the scalp by means of a concentric dual needle arrangement relying, however, on acceptance of the implanted plug.

Nate U.S. Pat. No. 3,858,245 discloses the utilization of individual suture loops which are sewn into the scalp and serve as anchors for attaching wefts of hair similar to Bauman.

Dick U.S. Pat. No. 3,914,801 also discloses forming suture loops in concentric circles on the scalp following which wefts of hair may be attached thereto.

Colone U.S. Pat. No. 4,027,675 discloses the implanting of loops of hair into the subcutaneous portion of the head with the ends of adjacent loops being tied together. However, these points of interconnection are external and would present obvious problems in grooming the hair.

Erb U.S. Pat. No. 3,596,292 discloses a hair implant method where the implanted hair has a percutaneous portion having elastic properties and a divergent cross-section for anchoring purposes.

Bennett U.S. Pat. No. 3,119,398 also discloses an implanting method wherein single strands of hair are processed so as to provide a nearly natural root structure to again assist in anchoring.

Popovics U.S. Pat. No. 1,059,631 primarily discloses an instrument for implanting hairs directly into the scalp in which small hooks are used to retain the hair.

Maxwell U.S. Pat. No. 3,062,214 also discloses apparatus for implanting the fibers, and particularly the ends thereof, directly into the scalp.

Barry U.S. Pat. No. 3,877,570 is another of the "hairpiece" approaches and discloses a sterile suture suitable for attaching hairpieces to the scalp.

Kost U.S. Pat. No. 3,513,860 discloses another method in which the hair is formed into U-shaped loops and the bases of the loops are pushed into the conventional base of a hairpiece in a straight line perpendicular to the base and applying adhesive or curing the base for permanent anchoring.

Smith U.S. Pat. No. 3,845,772 discloses a retention suture which possibly could be utilized in connection with treating baldness to prevent tearing of tissue when closing an incision, but is silent with regard to anchoring the actual strands beneath the scalp.

Kessler U.S. Pat. No. 3,908,674, discloses a method of securing hairpieces to cover a bald area of the scalp wherein sutures are permanently implanted within the scalp and held by washers and the hairpiece is secured thereto.

Sperling U.S. Pat. No. 3,755,824 discloses another method for avoiding the appearance of baldness wherein sutures are located permanently at strategic locations on the scalp and a scalp net is secured thereto.

Kohler U.S. Pat. No. 3,589,376 is essentially directed to a method of making wigs.

Rich U.S. Pat. No. 3,421,521 is also directed to a method of forming a hairpiece per se as in Mann U.S. Pat. No. 2,253,635.

Seiderman U.S. Pat. No. 2,636,460 discloses a process for manufacturing products simulating human or animal hair and its only pertinency is the fact that bunched loops are inserted into the base or scalp portion of the head using a trocar means.

Norwegian Pat. No. 30,751 is of some interest also in that two hairs are joined together at their root ends by a gold wire.

Nakayama U.S. Pat. No. 4,054,954 is also of interest in showing an endless suture which is embedded under the scalp and a plurality of rings threaded onto the suture which serve as anchoring means for a hairpiece.

While this prior art is illustrative of the several known methods of treating baldness, none of them however disclose the unique method disclosed herein by applicant wherein the hair can be firmly and securely implanted in the subcutaneous tissue beneath the scalp with its projecting ends assuming a relatively normal disposition above the surface of the scalp.

SUMMARY OF THE INVENTION

It has been found that improved results can be obtained in connection with the implantation of natural or artificial replacement hair by preferably pre-forming the strands of the hair to a looped or U-shaped configuration; securing the loop just formed to a penetration instrument or needle; inserting that instrument beneath the scalp in a curved path; disposing the strand of hair in the tissue in a more or less concave configuration with regard to the surface of the scalp and withdrawing of the needle.

It has also been found that this method can further be facilitated by applying a tissue adhesive to the base of the loop so as to assist in anchoring the same in the tissue.

Furthermore, it has been found that carrying out a method of this nature can be facilitated by providing a needle having a handle and an arcuate projecting end terminating in a sharp point capable of penetrating the scalp. It has also been discovered that a pocket can be provided rearwardly from the pointed end to receive the strands of hair and carry it into the tissue.

Furthermore, it has been discovered that a gripping handle can be employed to increase the mechanical advantage and precison of the operation by engaging the handle end of the needle.

It has also been discovered that provision of a hollow needle and hollow gripping handle will facilitate attachment of the gripping handle to a source of tissue adhesive or hemostatic fluid so that such fluid can be injected through the handle and the needle into the tissue adjacent the location of the implanted hair.

Furthermore, it has also been discovered that further improved results can be obtained by providing means for removing the hair from the carrying notch on the needle so as to insure that it remains in place upon withdrawal of the needle.

Accordingly then, production of an improved method and apparatus for treating baldness becomes the principal object of this invention with other objects hereof becoming more apparant upon a reading of the following brief specification considered and interpreted in view of the accompanying drawings.

OF THE DRAWINGS

BRIEF DESCRIPTION OF THE PREFERRED EMBODIMENTS

THE APPARATUS

It will first be noted that in describing the various embodiments of the method and apparatus of this invention reference will commonly be made to "strands" and it should be understood that in all instances such reference is intended to refer to both natural hair and synthetic fibers and is employed for the sake of brevity in this description.

Figure 1:
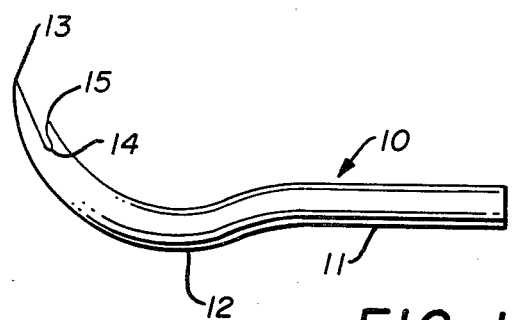
FIG. 1 is an elevational view of one form of needle employed in this invention.
Figure 4:
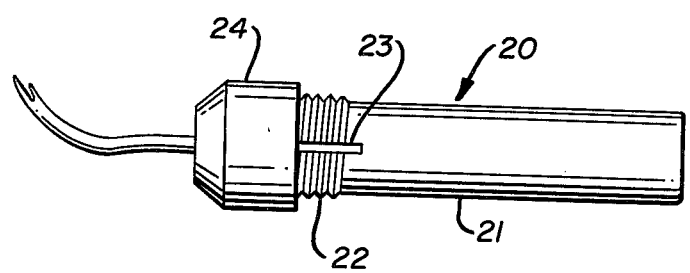
FIG. 4 is an elevational view showing the needle in place in the gripping handle.
Figure 11:
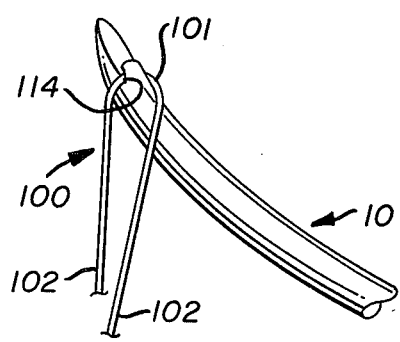
FIG. 11 is a perspective view showing the needle engaging a strand of hair.
Figure 13:
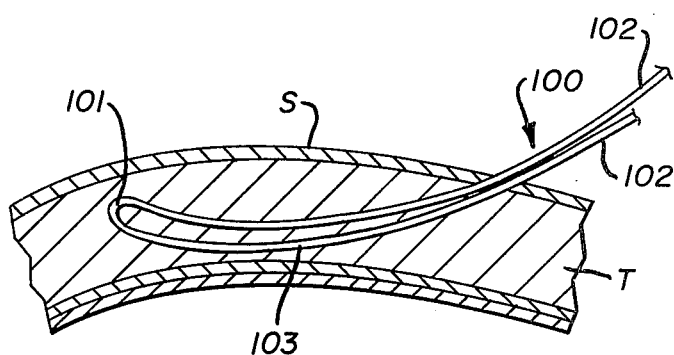
FIG. 13 is a view similar to FIG. 12.
Figure 12:
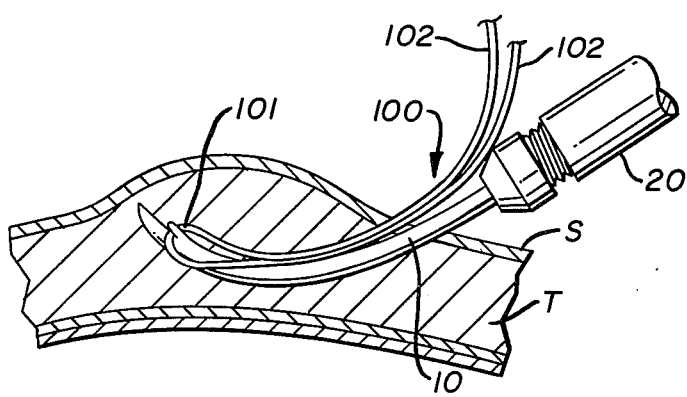
FIG. 12 is a sectional view showing the implantation of a strand of hair utilizing one of the gripping handles.
Figure 14:
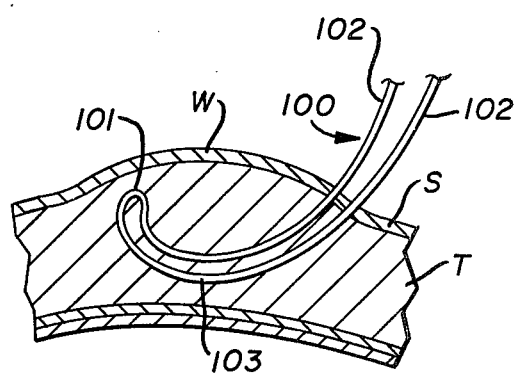
FIG. 14 is a view similar to FIG. 12 following removal of the needle.

Turning then to the drawings, it will be noted that the basic components of the apparatus necessary to carry out the method include a penetration instrument such as the needle 10 of FIG. 1, a gripping handle such as the handle 20 of FIG. 4 and the strand itself such as the strand 100 of FIG. 11.

Referring then to FIG. 1 for a description of the instrument or needle per se, it will be noted that the needle has an elongate shank portion 11 which terminates in an arcuate penetration portion 12 which in turn ultimately terminates in a pointed or beveled end 13. The needle is cut away rearwardly from the point 13 to form the pocket 14 with an overlying lip 15.

Figure 2:
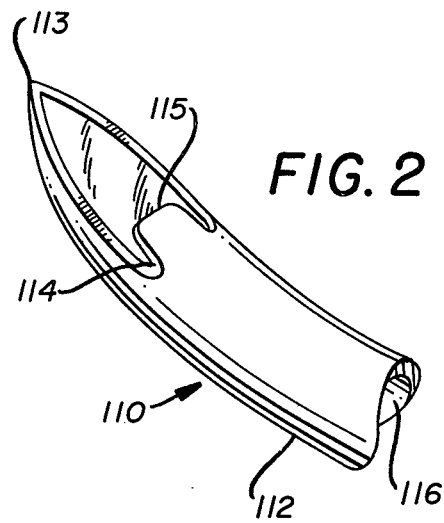
FIG. 2 is a partial perspective view of one form of the needle shown in FIG. 1.
Figure 3:
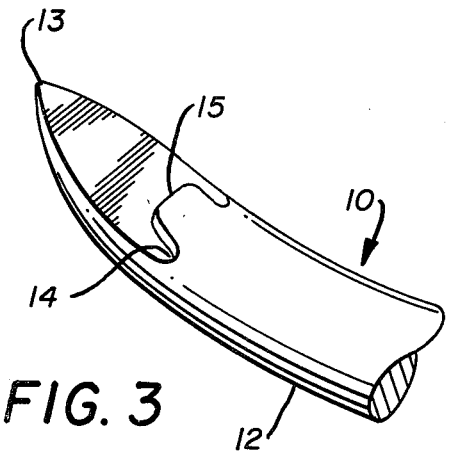
FIG. 3 is a partial perspective view of another form of the needle shown in FIG. 1.

The basic configuration of the needle is shown in FIG. 1 and reference will now be had to FIGS. 2 and 3 wherein partial perspective views are shown of the area adjacent the ultimate penetrating end 13 of two variations.

FIG. 3 shows a solid needle and the end 13 and penetration portion 12 are illustrated therein. FIG. 2 shows a hollow needle and in this instance the needle characteristics have been referred to by the numerals 110 through 116 with 116 indicating the hollow central bore or passageway. Similar characteristics are referred to by similar numbers in FIGS. 1 through 3 although numbers in the 100 series will be used throughout to refer to the hollow needle 110 while numerals in the 10 series will be used throughout to refer to the solid needle 10.

In any event, however, the basic components of the needle shown in FIGS. 2 and 3 are identical except for the fact that one is hollow and one is solid.

Figure 5:
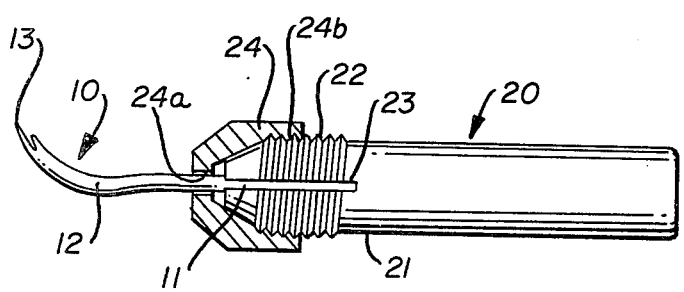
FIG. 5 is an elevational view similar to FIG. 4 partially in section.

Turning then to FIG. 4, it will be seen that a gripping handle 20 is provided with this handle having a body 21 terminating in a threaded end 22 and having opposed axially extending slots 22, 23 therein. Only one of these slots is shown in the view of this handle in FIGS. 4 and 5, but essentially they are slots cut inwardly in an axial direction from the left hand end of the handle.

The handle also includes a cap 24 which has a through aperture 24a sized so as to fairly snugly receive the shank 11 of the needle 10. The cap 24 also is threaded internally as at 24b so that, with the shank 11 inserted into the front end of the handle 20 and through the opening 24a of cap 24, the cap can be screwed down so as to essentially collapse the end of the handle about the slots 23 and grip the shank in place. This provides a the tissue and assist in the healing and anchoring to the strand 100.

Figure 6:
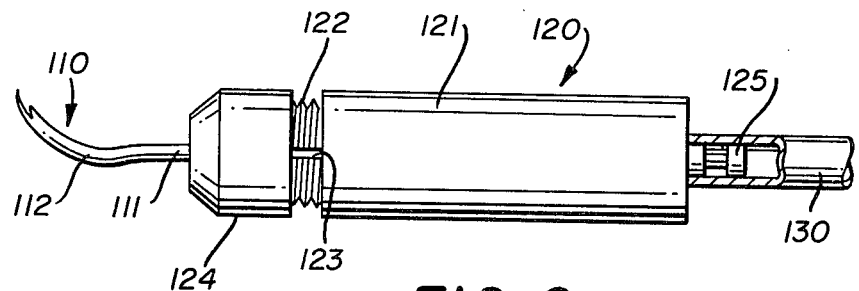
FIG. 6 is an elevational view of a modified form of gripping handle with the needle in place.
Figure 7:
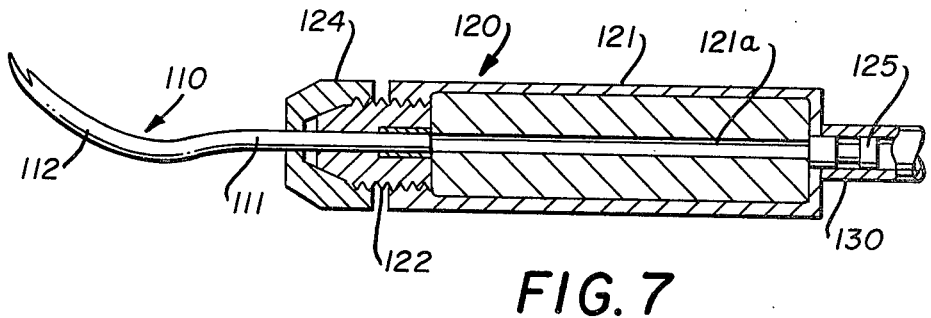
FIG. 7 is a view similar to FIG. 6 broken away in section.
Figure 8:
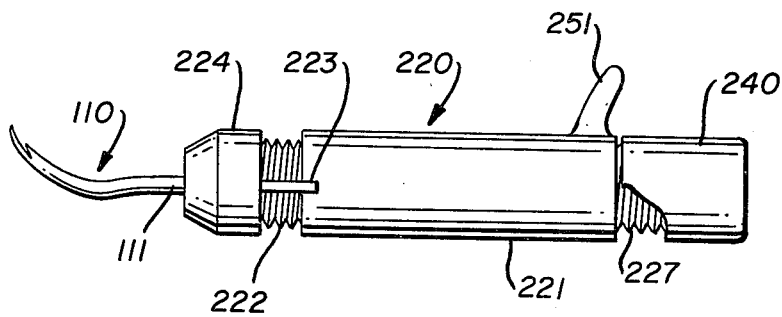
FIG. 8 is an elevational view of a further modified form of gripping handle with the needle in place.
Figure 9:
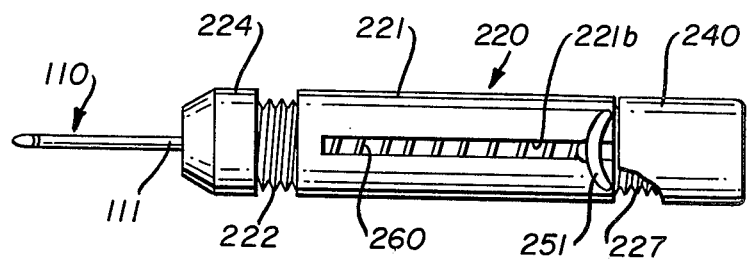
FIG. 9 is a top plan view of the gripping handle and needle assembly of FIG. 8.
Figure 10:
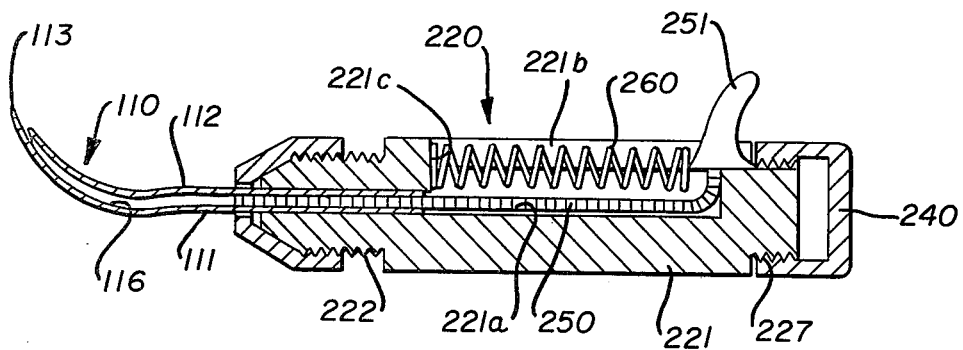
FIG. 10 is a view similar to FIG. 8 in section.
Figure 15:
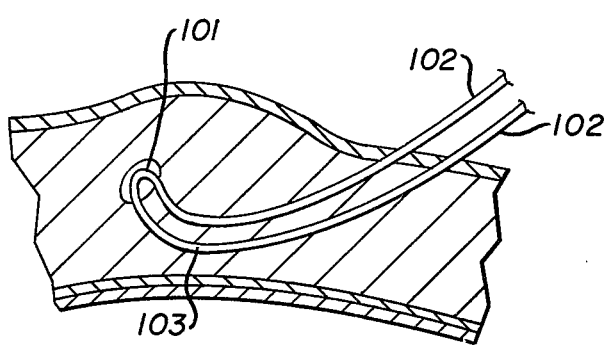
FIG. 15 is a view similar to FIG. 14 showing a modified form of the invention.

It is also possible, as illustrated in FIG. 15 to put tissue inert material or tissue adhesive on the base 101 of the loop prior to insertion in which event the hollow handle and hollow needle of FIGS. 6 and 7 would not be required.

While a full and complete description of the invention has been set forth in accordance with the dictates of the Patent Statutes, it should be understood that modifications can be resorted to without departing from the spirit hereof or the scope of the appended claims.

Figure 16:
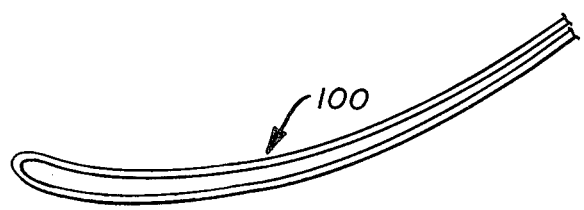
FIG. 16 is a view showing a pre-formed strand of hair according to this invention.

As noted earlier, in the preferred method the strand will be pre-formed to the condition of FIG. 16. However, due to the fact that the penetration path is arcuate or semilunar, the strand 100 will be placed in the tissue in the same configuration even if it is only formed as a loop when engaged with the needle. Under many circumstances this fact will be sufficient to achieve the objects of the invention.

It should also be noted that the instruments and apparatus illustrated and described herein can be utilized, as explained, regardless of whether the strand is pre-formed.

What is claimed is:

1. A method of implanting replacement hair in a human scalp comprising the steps of:
   (A) forming at least a first strand into a U-shaped loop having a base and free ends;
   (B) engaging the base of said loop with a penetration instrument having a body with an arcuate penetration portion terminating in a pointed end and having a generally circular cross-section portion;
   (C) penetrating the scalp in an arcuate path and positioning said strand in the subcutaneous tissue in arcuate configuration with its base disposed beneath the scalp at a point remote from the point of penetration, its free ends projecting above the scalp and at least a portion of said strand between said base and said free ends being disposed a greater distance beneath the scalp than said base;
   (D) withdrawing said instrument; and
   (E) repeating steps A through D until the desired density of scalp covering is achieved.

2. The method of claim 1 wherein said strand is pre-formed into a U-shaped loop having an arcuate configuration in elevation.

3. The method of claim 1 further characterized by the step of disengaging said strand from said instrument prior to removal thereof.

4. The method of claim 1 further characterized by the step of forming an elevation on the scalp prior to penetrating the scalp.

5. The method of claim 1 further characterized by the step of introducing a chemical agent through said penetration instrument adjacent the base of said strand after positioning thereof and prior to withdrawal of the instrument.

6. The method of claim 1 further characterized by the step of depositing a chemical agent on the base of the U-shaped loop formed by said strand prior to penetration and arcuate positioning thereof.

* * * * *